United States Patent
Gruenfeld et al.

[11] Patent Number: 5,842,996
[45] Date of Patent: Dec. 1, 1998

[54] AUTOMATIC TOURNIQUET SYSTEM

[75] Inventors: Frank Vincenz Jonas Gruenfeld, Rehovot; Alexander Opatowsky, Ra'anana; Joel Engel, Ramat Gan; Yehouda David, Savion; Ofer Levy, Mobile Post Soreq Vally, all of Israel

[73] Assignees: FMS-Future Medical System, S.A., Meyrin Geneva, Switzerland; Future Medical Systems, S.A., Saint-Jeannet, France

[21] Appl. No.: 530,317

[22] PCT Filed: Mar. 31, 1994

[86] PCT No.: PCT/EP94/01044

§ 371 Date: Jan. 22, 1996

§ 102(e) Date: Jan. 22, 1996

[87] PCT Pub. No.: WO94/22364

PCT Pub. Date: Oct. 13, 1994

[30] Foreign Application Priority Data

Apr. 4, 1993 [IL] Israel ........................................ 105306

[51] Int. Cl.[6] ...................................................... A61B 5/00
[52] U.S. Cl. ........................... 600/490; 606/202; 600/499; 600/492
[58] Field of Search ........................ 606/201.2; 128/686; 604/66; 600/490, 492, 493–496, 499

[56] References Cited

U.S. PATENT DOCUMENTS

| | | |
|---|---|---|
| 4,106,002 | 8/1978 | Hogue, Jr. . |
| 4,321,929 | 3/1982 | Lemelson et al. . |
| 4,469,099 | 9/1984 | McEwen . |
| 4,479,494 | 10/1984 | McEwen ................................. 606/202 |
| 4,520,819 | 6/1985 | Birmingham et al. . |
| 4,520,820 | 6/1985 | Kitchin et al. . |
| 4,548,198 | 10/1985 | Manes . |
| 4,635,635 | 1/1987 | Robinette-Lehman . |
| 4,637,394 | 1/1987 | Racz et al. . |
| 4,671,290 | 6/1987 | Miller et al. . |
| 4,691,738 | 9/1987 | McCune . |
| 4,773,419 | 9/1988 | Tountas . |
| 4,796,184 | 1/1989 | Bahr et al. . |
| 4,858,616 | 8/1989 | Samaras et al. ......................... 600/492 |
| 4,889,133 | 12/1989 | Nelson et al. ............................ 600/494 |
| 4,979,953 | 12/1990 | Spence . |
| 5,048,536 | 9/1991 | McEwen . |
| 5,069,219 | 12/1991 | Knoblich ................................. 600/492 |
| 5,181,522 | 1/1993 | McEwen . |
| 5,254,087 | 10/1993 | McEwen ................................... 604/66 |
| 5,352,195 | 10/1994 | McEwen ................................. 606/202 |

FOREIGN PATENT DOCUMENTS

| | | |
|---|---|---|
| 296635 | 12/1988 | European Pat. Off. . |
| WO 83/00995 | 3/1983 | WIPO . |
| WO 92/14409 | 9/1992 | WIPO . |

OTHER PUBLICATIONS

McEwen et al, "An adaptive Tourniquet for Improved Safety in Surgery," IEEE Transactions on Biomedical Engineering, vol. BME–29, No. 2, Feb. 1982.

Bussani, C.R. et al., Improved tracking of limb occlusion pressure for surgical tourniquets, *IEEE Transactions on Biomedical Engineering*, 1988, vol. 35, No. 4, pp. 221–228.

Levy, O., et al., Minimal tourniquet pressure to maintain arterial closure in upper limb surgery, *The Journal of Hand Surgery*, vol. 18B, No. 2, Apr. 1993, pp. 1–3.

Crenshaw, A.H., *Campbell's Operative Orthopaedics*, Eighth Edition, Mosby Year Book, St. Louis, vol. 1, pp. 3–4, vol. 5, pp. 2967–2969.

*Primary Examiner*—Robert L. Nasser
*Attorney, Agent, or Firm*—Young & Thompson

[57] ABSTRACT

An automatic tourniquet system (10) including variable pressure cuff apparatus (60) for applying a variable pressure to a limb or artery of a patient in order to occlude blood flow thereat and control apparatus (40) for determining the operative pressure of the variable pressure cuff (20) apparatus and including apparatus for estimating the minimum effective cuff pressure required for complete occlusion.

24 Claims, 8 Drawing Sheets

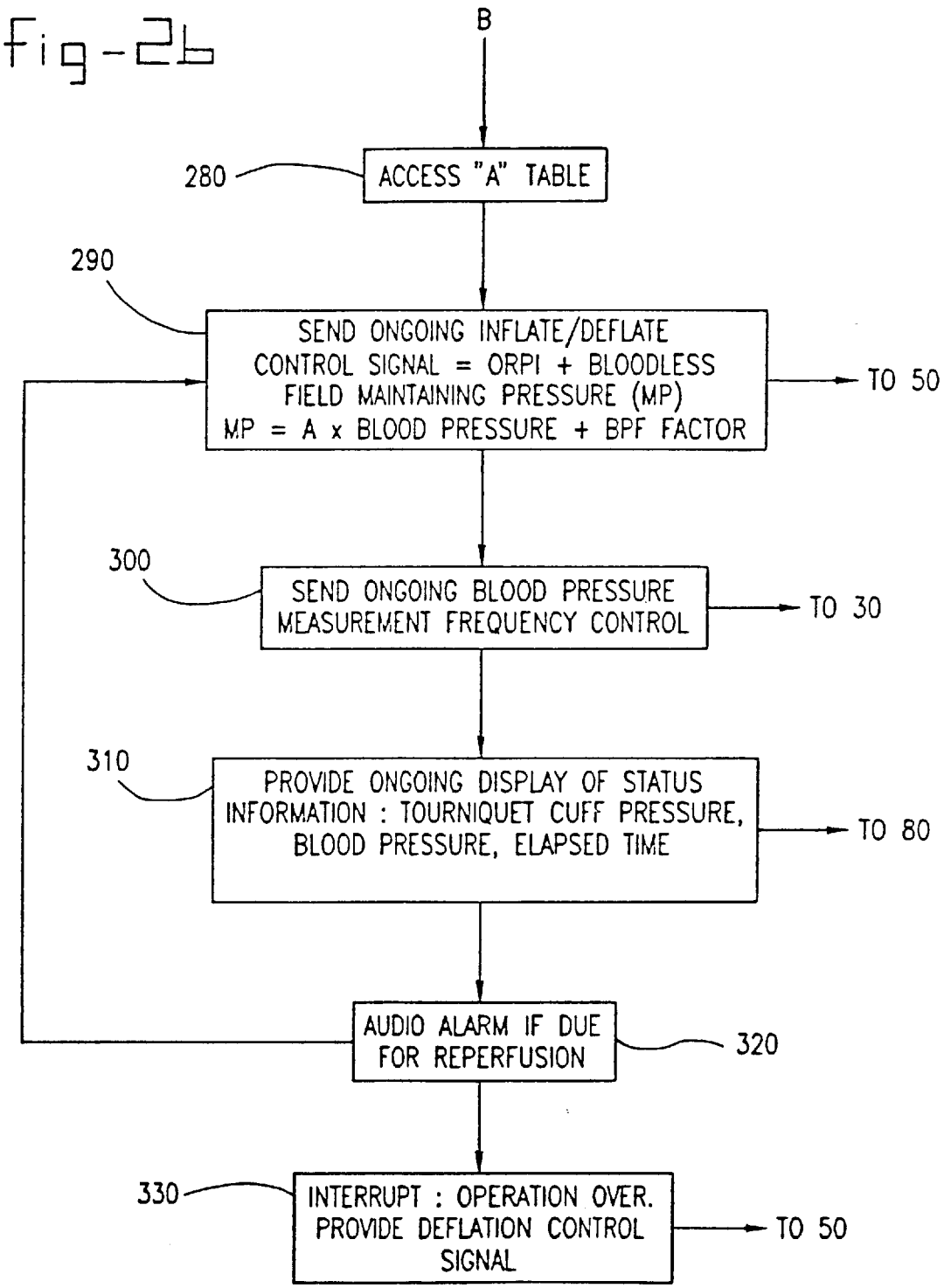

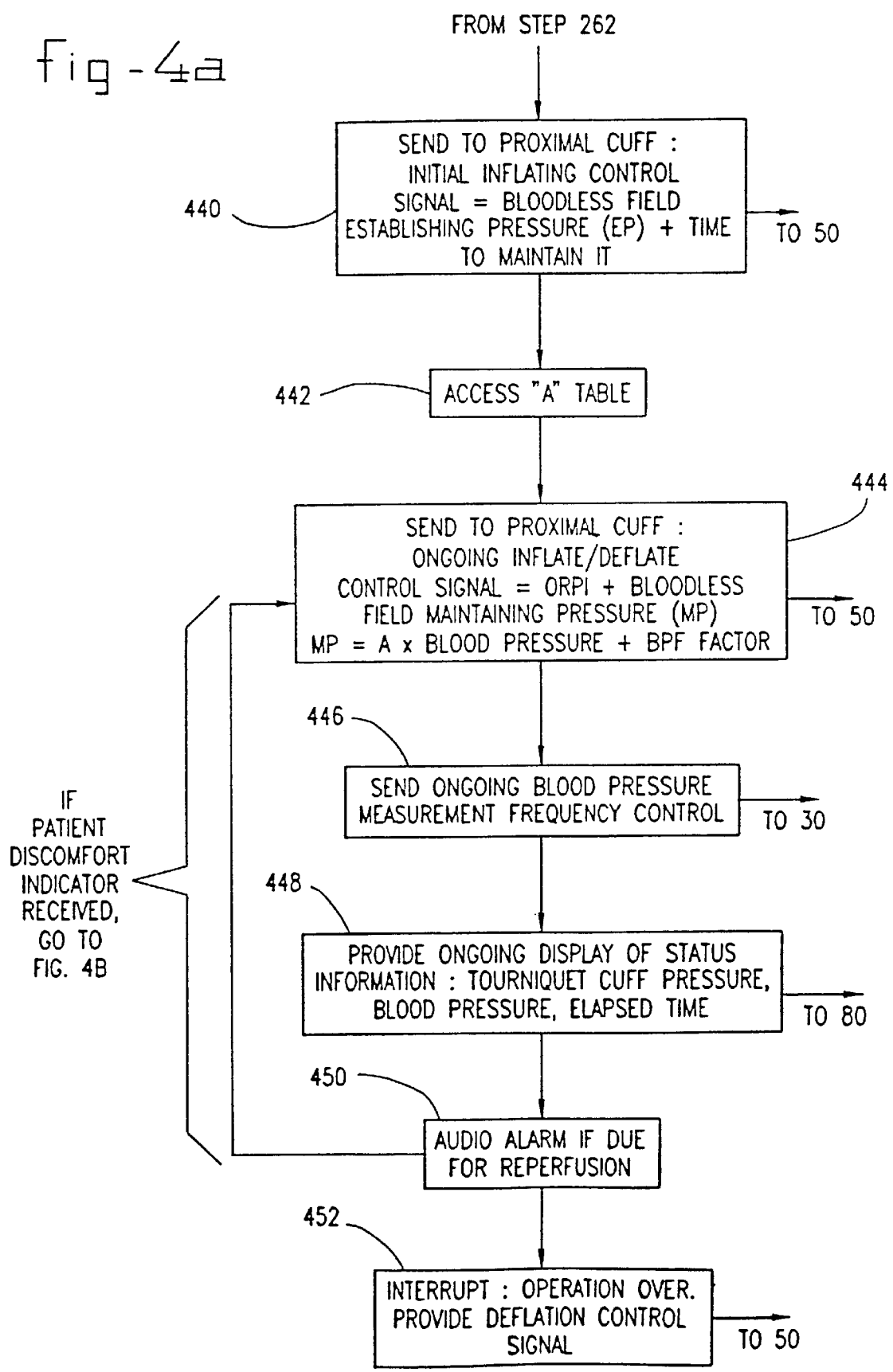

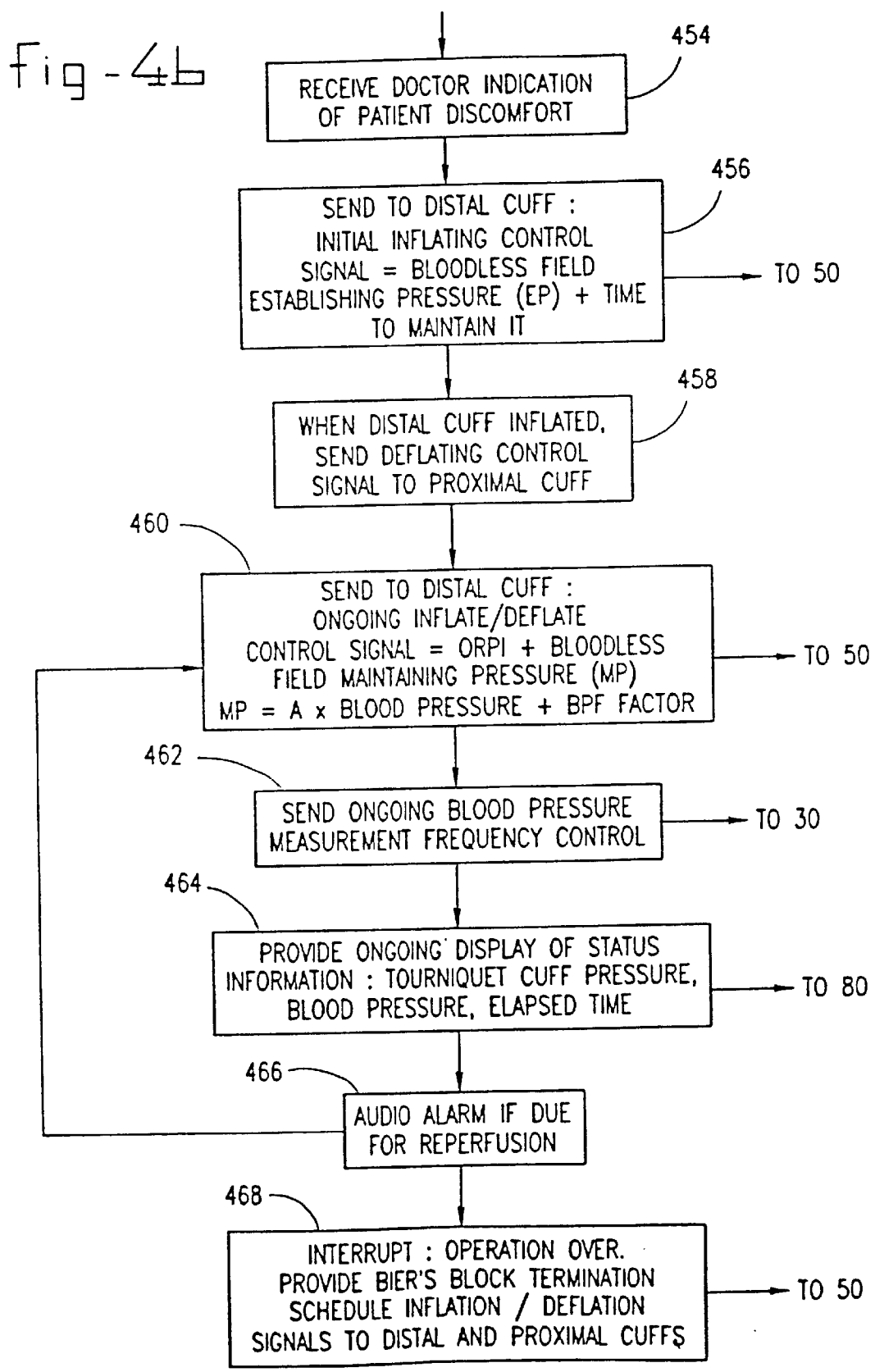

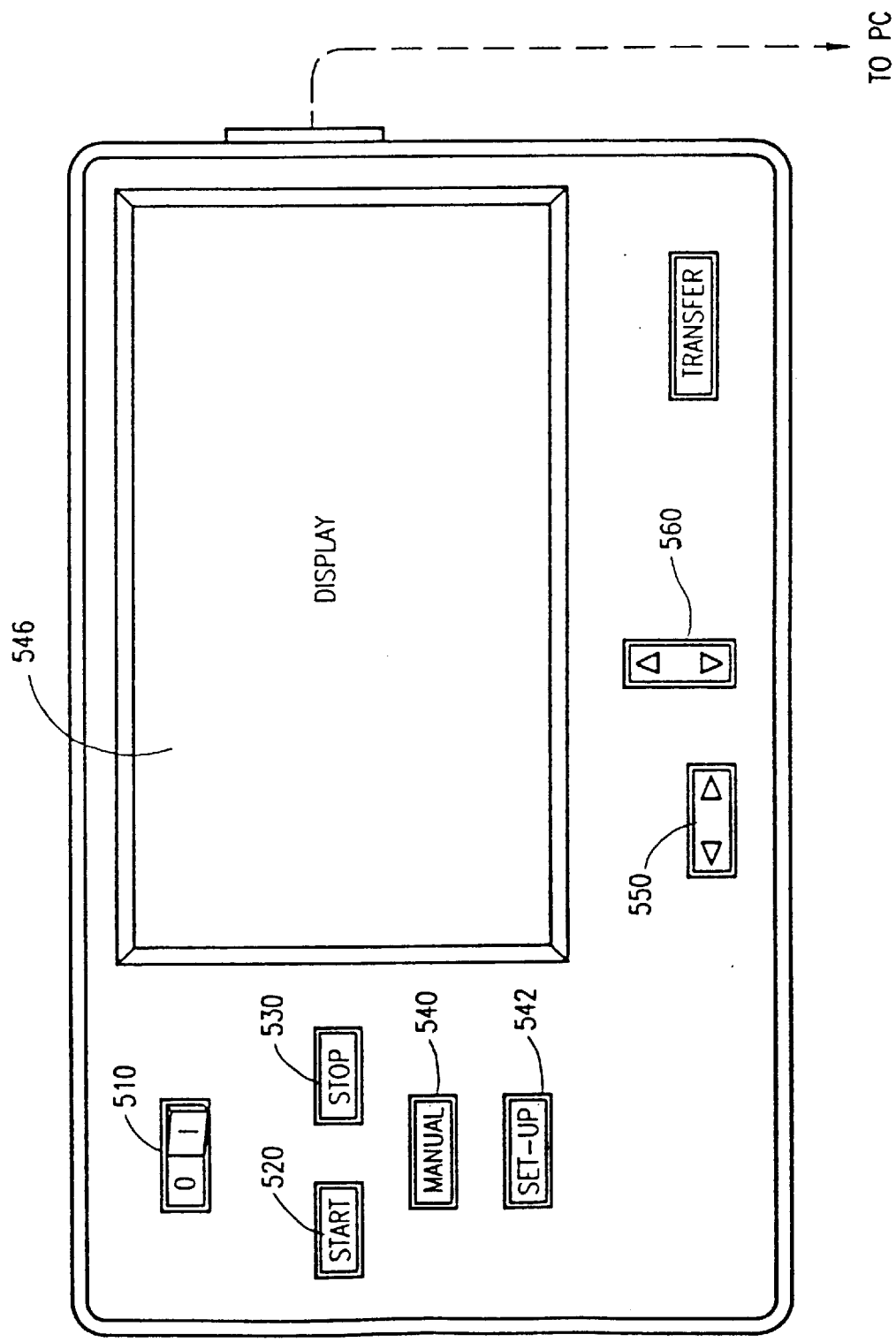

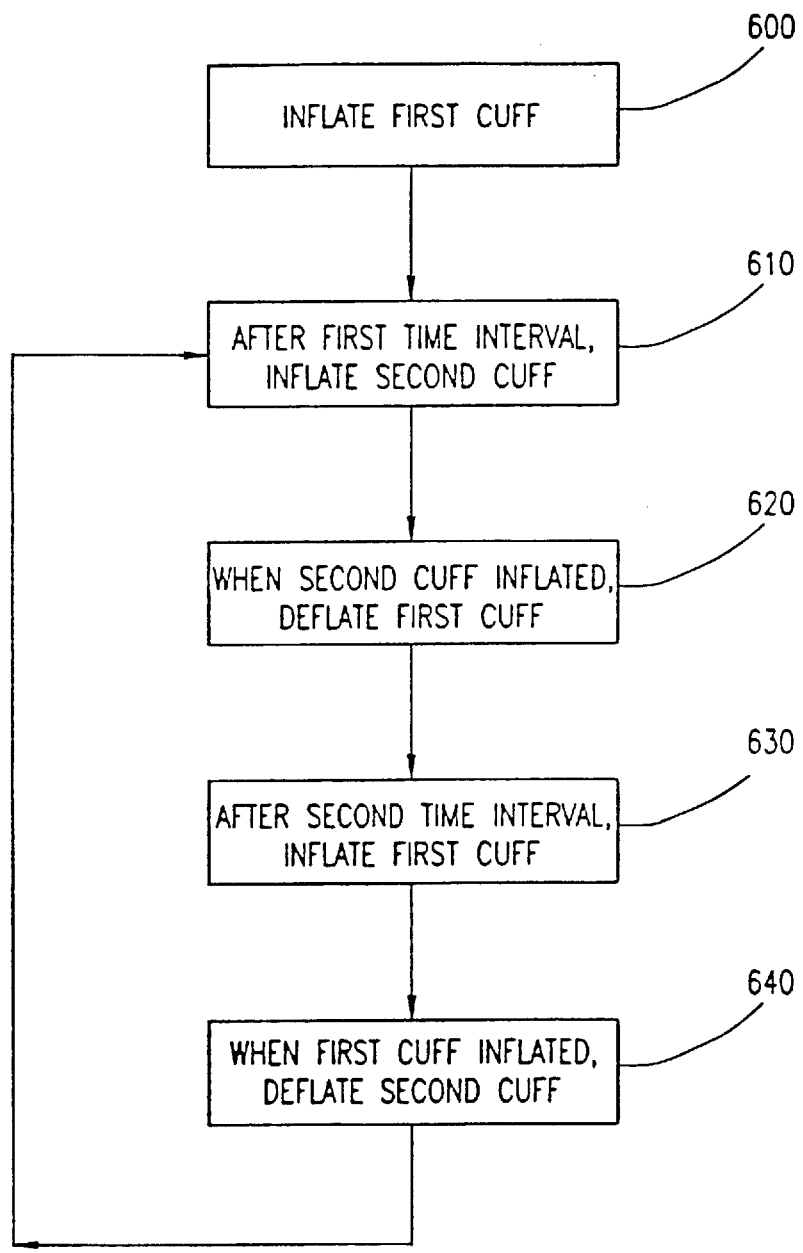

AUTOMATIC TOURNIQUET SYSTEM

FIELD OF THE INVENTION

The present invention relates to methods and apparatus for regulating tourniquet pressure.

BACKGROUND OF THE INVENTION

State of the art tourniquet systems are described in the following United States patents:

U.S. Pat. No. 4,106,002 to Hogue, Jr., U.S. Pat. No. 4,321,929 to Lemelson et al, U.S. Pat. No. 4,469,099 to McEwen, U.S. Pat. No. 4,479,494 to McEwen, U.S. Pat. No. 4,520,819 to Birmingham et al, U.S. Pat. No. 4,520,820 to Kitchin et al, U.S. Pat. No. 4,548,198 to Manes, U.S. Pat. No. 4,635,635 to Robinette-Lehman, U.S. Pat. No. 4,637,394 to Racz et al, U.S. Pat. No. 4,671,290 to Miller et al, U.S. Pat. No. 4,691,738 to McCune, U.S. Pat. No. 4,773,419 to Tountas, U.S. Pat. No. 4,979,953 to Spence, U.S. Pat. No. 5,048,536 to McEwen, U.S. Pat. No. 5,181,522 to McEwen.

SUMMARY OF THE INVENTION

The present invention seeks to provide an improved automated system for computing, establishing and maintaining suitable levels of tourniquet pressure.

There is thus provided, in accordance with a preferred embodiment of the present invention, an automatic tourniquet system including variable pressure cuff apparatus for applying a variable pressure to a limb or artery of a patient in order to occlude blood flow thereat and control apparatus for determining the operative pressure of the variable pressure cuff apparatus and including apparatus for estimating the minimum effective cuff pressure required for complete occlusion.

There is also provided, in accordance with another preferred embodiment of the present invention, automatic tourniquet system including variable pressure cuff apparatus for applying a variable pressure to a limb or artery of a patient in order to occlude blood flow thereat and control apparatus for determining the operative pressure of the variable pressure cuff apparatus and including apparatus for monitoring the blood pressure of a patient and apparatus for determining the operative pressure as the product of blood pressure and a factor.

Further in accordance with a preferred embodiment of the present invention, the blood pressure used in the apparatus for determining is a weighted combination of the systolic and diastolic blood pressures.

Still further in accordance with a preferred embodiment of the present invention, the factor is selected according to at least one of the following: the limb or artery on which the cuff apparatus is mounted, the size of the cuff apparatus, and whether the patient is an adult or a child.

Further in accordance with a preferred embodiment of the present invention, the control apparatus includes apparatus for causing the cuff apparatus to apply an initial pressure which is at least twice the blood pressure for a predetermined limited time.

Still further in accordance with a preferred embodiment of the present invention, the initial pressure is a constant for a limb/artery.

Further in accordance with a preferred embodiment of the present invention, the predetermined limited time is less than 10 minutes.

Still further in accordance with a preferred embodiment of the present invention, the weighted combination is the mean blood pressure.

Further in accordance with a preferred embodiment of the present invention, the apparatus for monitoring includes apparatus for measuring the systolic and diastolic blood measure.

There is also provided, in accordance with another preferred embodiment of the present invention, a tourniqueting method including the steps of:

a. providing two or more adjacent occlusive cuffs, b. inflating the first cuff, c. after a predetermined or user-selected time interval, inflate the second cuff, d. once the second cuff is inflated, deflate the first cuff, thereby relieving pressure on the first cuff body site, e. after a predetermined or user-selected time interval, inflate the first cuff, f. once the first cuff is inflated, deflate the second cuff, thereby relieving pressure on the second cuff body site, and g. if the operation has not yet terminated, repeat steps c–f until the operation is terminated, and h. upon receipt of an interrupt indicating that the operation is terminated, provide a deflation control signal to the inflated cuff or cuffs.

There is also provided, in accordance with another preferred embodiment of the present invention, an automatic tourniquet technique including the steps of applying a variable pressure to a limb or artery of a patient in order to occlude blood flow thereat and determining the operative pressure of the variable pressure cuff apparatus and including the steps of monitoring the blood pressure of a patient and setting the operative pressure as the product of blood pressure and a factor.

Further in accordance with a preferred embodiment of the present invention, the blood pressure used in the determining step is a weighted combination of the systolic and diastolic blood pressures.

Still further in accordance with a preferred embodiment of the present invention, the factor is selected according to the limb or artery on which the cuff apparatus is mounted.

Still further in accordance with a preferred embodiment of the present invention, the determining step includes causing the cuff apparatus to apply an initial pressure which is at least twice the blood pressure for a predetermined limited time.

Additionally in accordance with a preferred embodiment of the present invention, the initial pressure is a constant for a limb/artery.

Still further in accordance with a preferred embodiment of the present invention, the predetermined limited time is less than 10 minutes.

Additionally in accordance with a preferred embodiment of the present invention, the weighted combination is the mean blood pressure.

Further in accordance with a preferred embodiment of the present invention, the monitoring step includes measuring the systolic and diastolic blood measure.

In accordance with another preferred embodiment of the present invention, there is provided automatic tourniqueting apparatus for controlling inflation and deflation of two or more adjacent occlusive cuffs, including an occlusive cuff inflation/deflation signal generator operative to provide control signals suitable for implementing at least some of the steps of the following schedule:

a. inflating the first cuff, b. after a predetermined or user-selected time interval, inflate the second cuff, c. once the second cuff is inflated, deflate the first cuff, thereby relieving pressure on the first cuff body site, d. after a predetermined or user-selected time interval, inflate the first cuff, e. once the first cuff is inflated, deflate the second cuff, thereby relieving pressure on the second cuff body site, f. if the operation has not yet terminated, repeat steps c–f until the operation is terminated, and g. upon receipt of an interrupt indicating that the operation is terminated, provide a deflation control signal to the inflated cuff or cuffs.

There is also provided, in accordance with another preferred embodiment of the present invention, apparatus for automatically performing an IV regional anesthesia for use in conjunction with a double tourniquet cuff system including a proximal cuff and a distal cuff and a cuff inflation/deflation device, the apparatus including a double tourniquet cuff control unit operative to control the cuff inflation/deflation device according to a proximal and distal cuff inflation and deflation schedule.

Further in accordance with a preferred embodiment of the present invention, the schedule includes:

a. in response to a user's signal, proximal cuff inflation until a particular relatively high cuff pressure is reached, b. once a particular relatively low cuff pressure is reached, maintaining the low cuff pressure in the proximal cuff, c. in response to a user's signal, distal cuff inflation until a particular relatively high cuff pressure is reached, d. once a particular relatively low cuff pressure is reached, maintaining the low cuff pressure in the distal cuff, e. after the relatively high cuff pressure is reached in the distal cuff, entirely deflating the proximal cuff, and f. in response to a user's signal, on-and-off deflating the distal cuff.

Further in accordance with a preferred embodiment of the present invention, the distal cuff deflation schedule includes a schedule of alternating inflations and deflations of the distal cuff.

Still further in accordance with a preferred embodiment of the present invention, the inflation and deflation schedule is determined according to at least one user input.

Additionally in accordance with a preferred embodiment of the present invention, the at least one user input includes at least one of the following: determination of a relatively high pressure for at least one of the distal and proximal cuffs, indication of a limb/artery, cuff size.

There is further provided, in accordance with another preferred embodiment of the present invention, an automatic tourniquet system including a tourniquet control signal generator operative to provide a first control signal operative to induce a relatively high tourniquet pressure suitable for establishing a bloodless field and subsequently to provide a second control signal operative to induce a relatively low tourniquet pressure suitable for maintaining the bloodless field.

There is also provided, in accordance with another preferred embodiment of the present invention, automatic tourniqueting apparatus for controlling inflation and deflation of two or more adjacent occlusive cuffs, including an occlusive cuff inflation/deflation signal generator operative to provide control signals suitable for implementing at least some of the steps of the following schedule:

a. inflating the first cuff, b. after a predetermined or user-selected time interval, inflate the second cuff, c. once the second cuff is inflated, deflate the first cuff, thereby relieving pressure on the first cuff body site, d. after a predetermined or user-selected time interval, inflate the first cuff, e. once the first cuff is inflated, deflate the second cuff, thereby relieving pressure on the second cuff body site, f. if the operation has not yet terminated, repeat steps c–f until the operation is terminated, and g. upon receipt of an interrupt indicating that the operation is terminated, provide a deflation control signal to the inflated cuff or cuffs.

BRIEF DESCRIPTION OF THE DRAWINGS

The present invention will be understood and appreciated from the following detailed description, taken in conjunction with the drawings in which:

FIGS. 2A and 2B, taken together, are a simplified flowchart of the operation of operation and control unit of FIG. 1;

FIGS. 4A and 4B, taken together, are a simplified flowchart of a branch of the flowchart of FIGS. 2A and 2B, for an instance in which a Bier's block procedure is to be performed;

FIG. 5 is a pictorial illustration of a display and control panel forming part of the user input and display panel unit of FIG. 1; and FIG. 6 is a simplified flowchart of a method for using a plurality of occlusive cuffs to maintain a bloodless field for an extended period of time without pressuring a single site for an extended period of time.

DETAILED DESCRIPTION OF PREFERRED EMBODIMENTS

Figure 1:
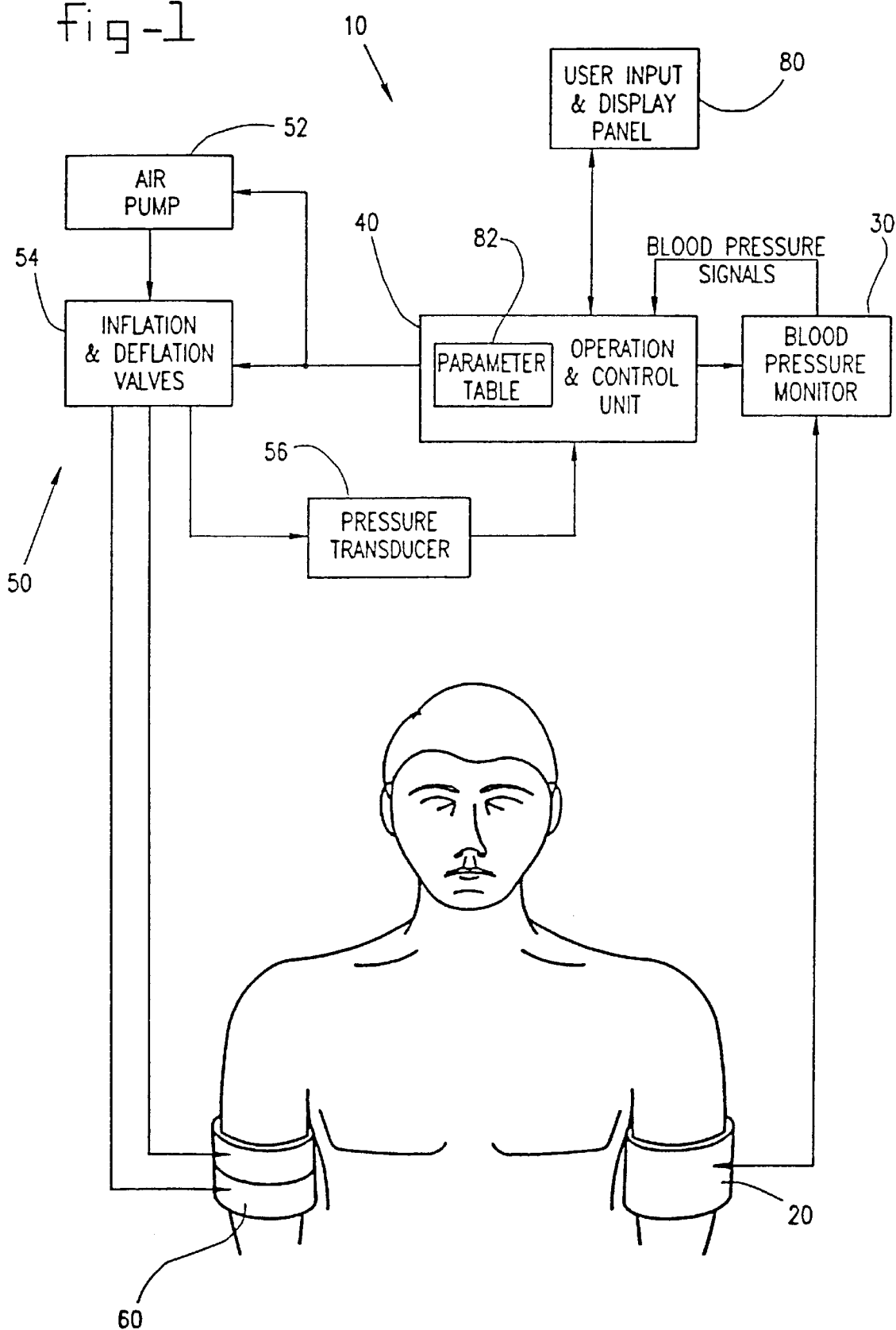
FIG. 1 is a simplified block diagram illustration of a tourniquet pressure regulating system constructed and operative in accordance with a preferred embodiment of the present invention which communicates with an external supply of compressed air.

Reference is now made to FIG. 1 which is a simplified block diagram illustration of a tourniquet pressure regulating system, referenced generally 10, which is constructed and operative in accordance with a preferred embodiment of the present invention.

The tourniquet pressure regulating system 10 includes a blood pressure transducer 20, which typically comprises a commercially available occlusive cuff and is operative to provide an indication of blood pressure.

The blood pressure indication provided by blood pressure transducer cuff 20 is provided to a blood pressure monitor 30 which is operative to provide a display and/or an output indication of at least one blood pressure characteristic which may be the output of blood pressure transducer 20 or some parameter or characteristic computed or generated therefrom. For example, the blood pressure monitor 30 may provide an output indication of mean blood pressure, namely, the following weighted combination:

$\frac{1}{3} \times$ systolic blood pressure $+ \frac{2}{3} \times$ diastolic blood pressure A commercially available system including a blood pressure transducer cuff and a blood pressure monitor is the DINAMAP Vital Signs Monitor, Model 8100, commercially available from Critikon, Inc., Tampa, Fla., USA.

Principles of operation of blood pressure monitors are described in *Monitoring in anesthesia and critical care medicine,* 2nd Ed., Casey D. Blitt, M. D., Churchill Livingstone, 1990.

Blood pressure signals are provided by the blood pressure monitor 30 to an operation and control unit 40 which is operative to provide the following information:

a. The operation and control unit 40 provides, to a pressurized gas supply system 50, an estimate of a minimum effective tourniquet pressure required to maintain an established bloodless field.

b. The operation and control unit 40 preferably inspects the blood pressure profile and particularly the rapidity of fluctuation thereof and provides to blood pressure monitor 30 an indication of a suitable time interval for blood pressure measurement, indicating how frequently it is necessary to measure blood pressure.

c. If the operation and control unit 40 receives an indication from a user that a IV regional anesthesia (Bier's block) procedure is to be performed, the operation and control unit 40 controls operation of pressurized gas supply system 50 so as to provide appropriate pressures for each of the two tourniquet cuffs employed in a Bier's block procedure, according to an appropriate schedule which preferably responds to a user's input.

Considerations in selecting appropriate timing and pressures for each stage of a Bier's block procedure are described in Crenshaw, A. H., (Ed.), *Campbell's operative orthopedics,* page 2967, 8th Ed., Mosby-Year Book, St. Louis, Mo., 1992.

Pressurized gas supply system 50 typically comprises an air pump 52, an associated valve system 54 and a pressure transducer 56.

Pressurized gas supply system 50 provides inflation and deflation of a tourniquet cuff 60. Tourniquet cuff 60 may comprise any commercially available tourniquet cuff such as one of the series of reusable tourniquet cuffs, commercially available from Smith & Nephew Richards Inc., Memphis, Tenn., USA or such as one of the series of disposable tourniquet cuffs, commercially available from Smith & Nephew Richards. Alternatively, tourniquet cuff 60 may comprise a dual cuff suitable for performing Bier's block procedures, i.e. IV regional anesthesia procedures. Dual cuffs are also commercially available from Smith & Nephew Richards.

According to a preferred embodiment of the present invention, the user of the system 10 may select any of a plurality of cuffs, varying in size, such as cuffs within a single series, to implement tourniquet cuff 60 and the operation and control unit 40 takes into account the size of the cuff as indicated by the user when estimating the minimum effective tourniquet pressure, all of which are provided integrally with the system.

It is appreciated that blood pressure cuff 20 and tourniquet cuff 60 may either be on the same limb or on opposite limbs. Alternatively, the two cuffs 20 and 60 may be replaced by a single double-module cuff which performs the blood pressure measurement function of cuff 20 and the tourniquet function of cuff 60.

A preferred method for implementing operation and control unit 40 is described below in further detail with reference to FIGS. 2A and 2B.

Operation and control unit 40 is associated with a user input and display panel 80. A description of a preferred configuration for panel 80 is provided below with reference to FIG. 5.

Figure 2A:
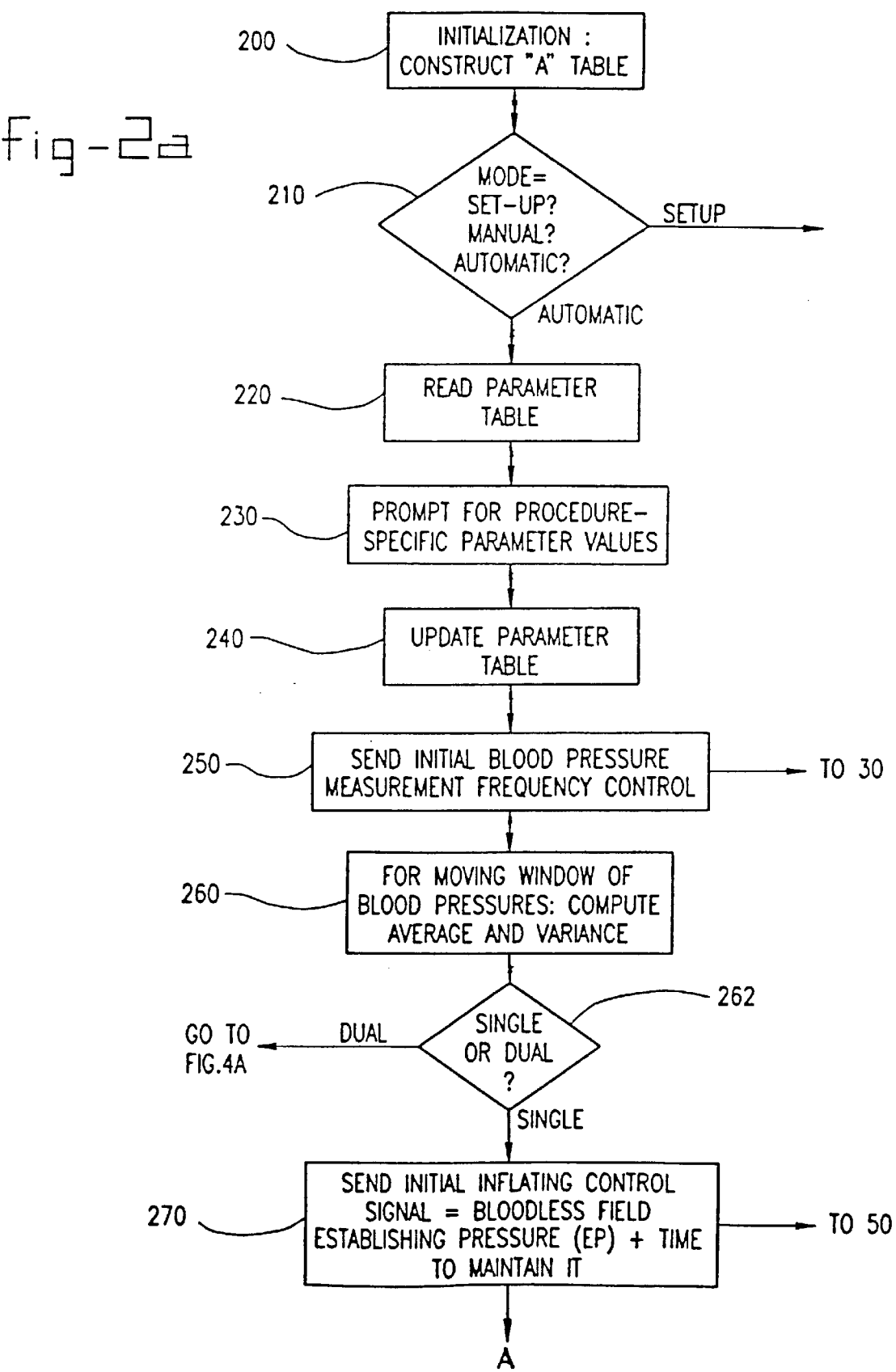

Reference is now made to FIGS. 2A and 2B which, taken together, are a simplified flowchart showing operation of the operation and control unit 40 of FIG. 1 for instances in which the user has indicated that a single cuff procedure, rather than a Bier's block double cuff procedure, is being employed.

Step 200: This initialization step is preferably performed prior to any operational use of the unit 40. In the course of experimental work, the inventors discovered that a good tourniquet cuff pressure value for maintaining an already established bloodless field may be computed by multiplying ongoing readings of blood pressure, such as mean blood pressure readings, by a factor which depends on the type of limb, the size of tourniquet cuff and, typically, the age group (adult/pediatric)

In step 200, a table is constructed which stores values for the above constant, termed herein A, for a variety of limb types, tourniquet cuff sizes, and, preferably age groups.

A preferred method for performing step 200 is described below with reference to FIG. 3.

Step 210: Determine which of the following modes has been selected by the user: set-up/manual/automatic. The flowchart below assumes that the automatic mode has been selected.

If the manual mode has been selected, a non-automatic procedure for controlling tourniquet pressure may be employed by the present apparatus, such as providing control signals which are based on user-selected or system default values. Typically, the user may select a manual work mode at any point in the course of using the system, at which point the system abandons the computations described below and makes a gradual transition to user-selected constant tourniquet pressure values.

If the set-up mode has been selected, unit 40 prompts the user through a set-up session in which the user is prompted to define each of a plurality of general parameters which are stored in a parameter table 82 (FIG. 1), such as the following parameter table:

| PARAMETER TABLE |  |
|---|---|
| I. GENERAL | |
| BLOODLESS FIELD ESTABLISHING PRESSURE -- ARM -- 300 | |
| BLOODLESS FIELD ESTABLISHING PRESSURE -- LEG -- 500 | |
| BLOODLESS FIELD ESTABLISHING PRESSURE -- MAJOR ARTERY--300 | |
| OPERATOR REQUESTED PRESSURE INCREMENTS (ORPI'S): | |
| ARM --   SINGLE CUFF: | 0 |
| PROXIMAL DUAL CUFF: | 0 |
| DISTAL DUAL CUFF: | 0 |
| LEG --   SINGLE CUFF: | 0 |
| PROXIMAL DUAL CUFF: | 0 |
| DISTAL DUAL CUFF: | 0 |
| MAJOR ARTERY | |
| SINGLE CUFF: | 0 |
| PROXIMAL DUAL CUFF: | 0 |
| DISTAL DUAL CUFF: | 0 |
| TIME TO ELAPSE UNTIL REPERFUSION OF ARM | 60 |
| TIME TO ELAPSE UNTIL REPERFUSION OF LEG | 60 |
| II. PROCEDURE-SPECIFIC | |
| LIMB (ARM/LEG/MAJOR ARTERY) | |
| CUFF (SINGLE/DUAL) | |
| CUFF SIZE | |
| PATIENT AGE GROUP (ADULT/PEDIATRIC) | |

During set-up, the user is prompted to select a pressure with which a bloodless field is to be established in the arm, in the leg and in a major artery. The user is also preferably prompted to select "operator requested pressure increments" (ORPI's), both for single cuff procedures and for each of the proximal and the distal cuffs employed in Bier's block procedures.

The ORPI's may be selected differently for the arm, for the leg and for a major artery. These increments are intended to allow a user to partially override the system by providing a higher bloodless field maintaining tourniquet pressure than that which the system would otherwise provide. Specifically, the system adds the appropriate ORPI to its own estimation of the minimum tourniquet pressure required to maintain a bloodless field.

The user also preferably selects a maximum time after which it is believed desirable to perform reperfusion. The system preferably provides an audio alarm to indicate that this time has elapsed.

Until the user chooses to select a value for any of the above parameters, the most recently selected previous value is stored in the parameter table 82. Initially, system default values are stored in the parameter table 82, such as the values indicated in the above parameter table. Pressure values are given in units of mm Hg. Time values are given in minutes.

Step 220: Read the general parameters from the parameter table 82.

Step 230: If a start key has been punched on the display and user input panel 80 of FIG. 1, the system prompts the user to provide at least one procedure-specific value which characterizes an individual operation on an individual patient, such as the following:
  i. type of limb—arm or leg or major artery
  ii. type of cuff—single or dual. A dual cuff procedure is also termed herein a Bier's block procedure.
  iii. cuff dimensions or cuff size.
  iv. patient age group. Typically age groups include a single adult age group and one or more pediatric age groups.

Step 240: Update the parameter table 82 according to the inputs received in step 230.

When the start button is pressed again:

Step 250: Provide a control indication to blood pressure monitor 30 including an indication of a time interval between blood pressure measurements, such as the minimum time interval supported by the blood pressure monitor 30, or approximately 2–2.5 minutes.

Step 260: Receive mean blood pressure measurements from blood pressure monitor 30 and conduct an ongoing analysis thereof, including continuous computations of the average mean blood pressure and of the variance of the blood pressure, over a moving window of, typically, 5 measurements.

Step 262: If the parameter table 82 indicates that a single cuff procedure is being followed, go to step 270. Otherwise, go to FIG. 4A.

Step 270: Provide an initial inflating control indication to pressurized gas supply system 50 including the bloodless field establishing pressure stored in the table 82, also termed herein the EP, and a time interval during which the establishing pressure is to be applied. Typically, the time interval is predetermined. A suitable value is, for example, 3 minutes.

A particular feature of the present invention is that, once a bloodless field has been established, the tourniquet cuff pressure is reduced so that a lower value is used to maintain the bloodless field than is used to establish the bloodless field.

Step 280: An appropriate A value is read from the A table constructed in step 200, according to the following procedure-specific parameters read from the parameter table 82: limb, cuff size, patient age group.

Step 290: On an ongoing basis, such as at the same frequency at which blood pressure is being measured, an inflating or deflating control signal is provided to pressurized gas supply system 50 of FIG. 1. The inflation/deflation control signal indicates the extent of inflation/deflation required to move from the current tourniquet pressure in tourniquet 60 to a newly computed tourniquet pressure. The system-computed tourniquet pressure comprises an estimated minimum pressure required to maintain a bloodless field (MP), to which is preferably added the user-selected ORPI value.

The MP value is estimated as follows:
  a. The current mean blood pressure is multiplied by the A value accessed in step 280.
  b. Optionally, the product computed in substep a is incremented by a blood pressure fluctuation (BPF) factor. The BPF factor may be established during initialization for each of a plurality of blood pressure variances and for each of a plurality of blood pressure measurement frequencies, and may be stored in a table. The BPF factor table may then be accessed as a function of the current blood pressure measurement frequency (step 300) and of the current blood pressure variance as computed in step 260. Typically, the BPF factor is large to the extent that the blood pressure variance is large and the blood pressure measurement frequency is small.

For example, the BPF factor may be a constant which is determined in step 422 of FIG. 4 for each age group, limb type and cuff size.

Each entry in the BPF factor table is selected such that fluctuations of more than a predetermined number of standard deviations will not occur, at a predetermined statistical confidence level. For example, the BPF factor value may be selected so as to prevent fluctuations of more than two standard deviations at a level of confidence of 95%.

Fluctuations in blood pressure may be forecasted by use of exponential smoothing, which is a known statistical technique.

Step 300: (optional) On an ongoing basis, such as once per blood pressure measurement, starting from after the first 3 or 5 blood pressure measurements, a signal indicative of an appropriate blood pressure measurement frequency is transmitted to blood pressure monitor 30 of FIG. 1. If the variation of the current blood pressure measurement, as computed in step 260, is large, the signal indicates that the blood pressure measurement frequency should increase, and conversely, if the variation is small, the blood pressure measurement frequency may be decreased.

Preferably, the recommended blood pressure measurement frequency is computed as follows:
  a. Fluctuations in blood pressure are forecasted by use of exponential smoothing.
  b. A frequency is selected such that fluctuations of more than a predetermined number of standard deviations will not occur, at a predetermined statistical confidence level, before the next blood pressure measurement. For example, the frequency may be selected so as to prevent fluctuations of more than two standard deviations at a level of confidence of 95%.

Step 310: Preferably, status information is displayed on display panel 80 of FIG. 1, such as indications of current tourniquet cuff pressure, current mean blood pressure, time remaining until reperfusion.

Step 320: If the time elapsed since the second time the start button is pressed exceeds the reperfusion time interval defined in the parameter table 82, an alarm is provided, such as an audio alarm.

Step 330: Once the user indicates, as by using stop key 530 of panel 80 of FIG. 5, that the surgical procedure has been completed, a suitable deflation control signal is provided to pressurized gas supply system 50. For example, the deflation control signal may comprise a signal to deflate the cuff.

Figure 3:
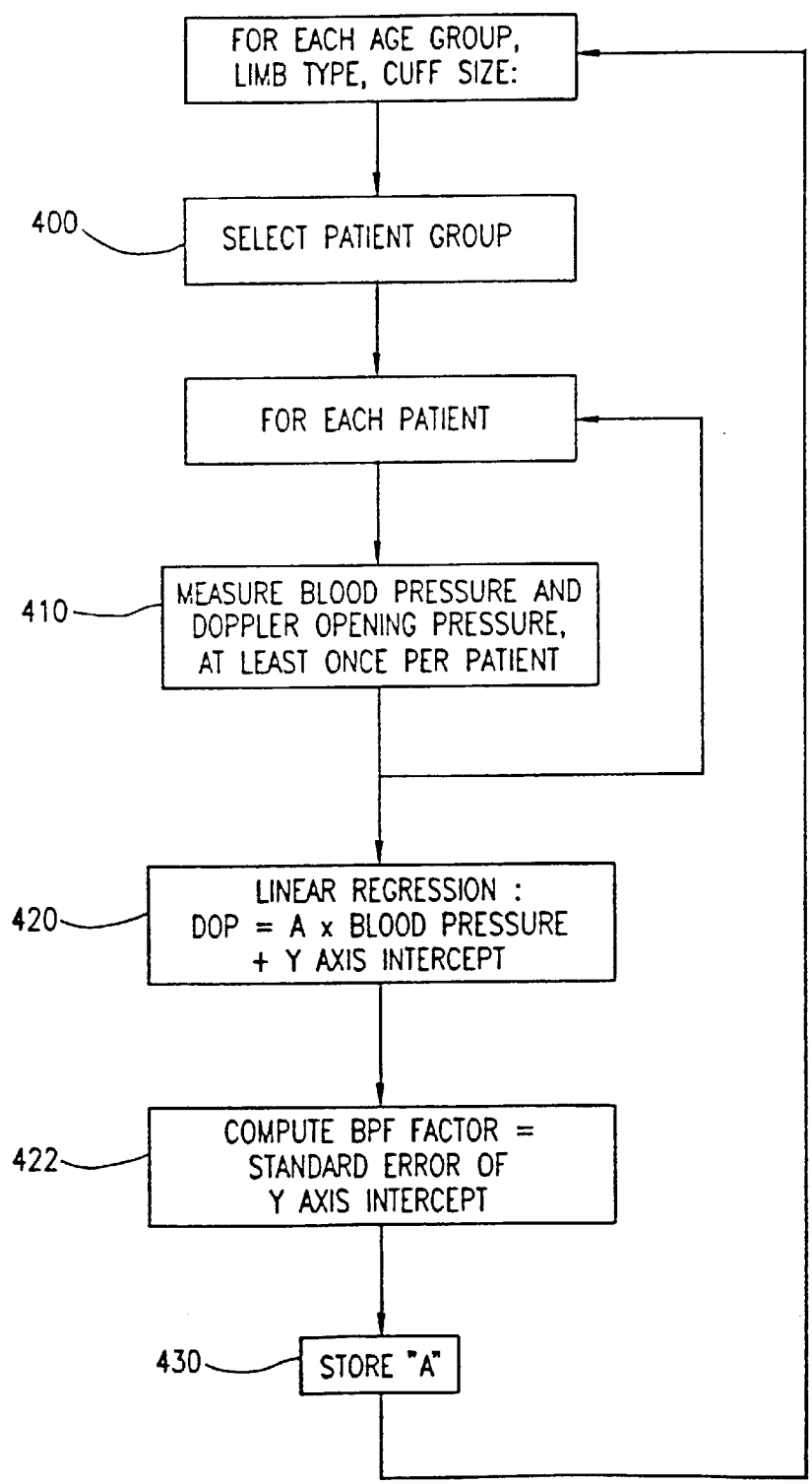
FIG. 3 is a simplified flowchart of a preferred method for performing an initialization step in the flowchart of FIGS. 2A and 2B.

FIG. 3 is a preferred method for implementing initialization step 200 of FIG. 2A in which a look-up table for the "A" parameter is constructed.

The following steps are performed for each entry in the look-up table, i.e. for each type of limb (arm/leg/major artery), for each tourniquet cuff size, and for each age group (adult and at least one pediatric age group).

Step 400: Select a sample of approximately 400 patients which is representative of the patients within the age group as to sex, age and medical condition.

For each patient,

Step 410: Take approximately 3 measurements, separated by 15 minute time intervals, of blood pressure and of Doppler opening pressure (DOP).

Step 420: Conduct a linear regression analysis (N=3× 400=1200), using the Doppler opening pressure as the predicted variable and the average blood pressure as the predicting variable. The A value for the individual entry is the slope of the linear regression.

Step 422: It is believed that a suitable method for computing the BPF factor employed in step 290 is by computing the standard error of the Y axis intercept for each age group, limb type and cuff size.

Step 430: Store the A value of step 420 in the location in the A table which corresponds to the individual limb, cuff size and, preferably, age group.

For example, a suitable value of A, for the arm, for a cuff of width 5.5 cm and for an adult population is 2.04.

Reference is now made to FIGS. 4A–4B which, taken together, comprise a preferred method for implementing operation and control unit 40 for instances in which the user has indicated, in step 262 of FIG. 2A, that a Bier's block dual cuff procedure is being employed. If the user has so indicated, the method of FIG. 4A may be employed. If the flow of FIG. 4A is interrupted by a patient discomfort indicator, such as via the "start" button 520 of FIG. 5, the method of FIG. 4B may be employed.

FIG. 5 is a pictorial illustration of user input and display panel of FIG. 1. The display and control panel of FIG. 5 preferably includes the following elements:

a. An on/off button 510. When the button 510 is in its on position, the system is in stand-by mode and awaits further inputs.

b. A start button 520;

c. A stop button 530;

d. A "manual" button 540 enabling the user to select a manual mode of operation;

e. A "set-up" button 542 enabling the user to select a set-up mode of operation;

f. a display panel 546;

g. An input value selecting mechanism such as a scroll 550 which allows a user to indicate whether he wishes to increase or decrease an existing numerical value.

h. A prompt scroll 560 which allows a user to indicate that the next prompt should be displayed on display 546.

It is appreciated that, more generally, all references above to "mean blood pressure" may be replaced by any suitable combination of the systolic and diastolic blood pressures.

It is appreciated that the invention shown and described herein is useful for providing tourniqueting for any or all limbs of a patient and/or occlusion of one or more arteries of a patient during any vascular surgical procedure which requires tourniqueting or occlusion.

It is appreciated that the apparatus of the present invention may be employed to provide computerized control of any suitable tourniqueting schedule. For example, it may be desired to provide a bloodless field using two or more adjacent occlusive cuffs, according to a schedule shown in FIG. 6:

a. inflate the first cuff;

b. after a predetermined or user-selected time interval, inflate the second cuff;

c. once the second cuff is inflated, deflate the first cuff, thereby relieving pressure on the first cuff body site;

d. after a predetermined or user-selected time interval, inflate the first cuff;

e. once the first cuff is inflated, deflate the second cuff, thereby relieving pressure on the second cuff body site;

f. repeat steps b–e until the operation is terminated.

g. Upon receipt of an interrupt indicating that the operation is terminated, provide a deflation control signal to the inflated cuff or cuffs.

Preferably, once an individual cuff has been inflated, an ongoing control signal is provided, as described above with reference to FIG. 3, according to which a relatively low tourniquet pressure is provided, just enough to maintain the bloodless field. This relatively low pressure is typically determined according to an ongoing indication of blood pressure, as described above with reference to FIG. 3.

The above schedule has the advantage of allowing a bloodless field to be maintained for a long time period, however, pressure on each individual tourniqueted location is provided only a portion of the time period, such as half of the time period. The above schedule is particularly useful in applications wherein anesthetic is provided proximally of the tourniqueted areas, such as in procedures carried out under general anesthesia.

It is appreciated that various features of the invention which are, for clarity, described in the contexts of separate embodiments may also be provided in combination in a single embodiment. Conversely, various features of the invention which are, for brevity, described in the context of a single embodiment may also be provided separately.

It will be appreciated by persons skilled in the art that the present invention is not limited to what has been particularly shown and described hereinabove. Rather, the scope of the present invention is defined only by the claims that follow:

We claim:

1. An automatic tourniquet system comprising:

variable pressure cuff means for applying a variable pressure to a limb or artery of a patient in order to occlude blood flow thereat, tourniquet control signal generator, which is connected to the cuff means and which is operative to provide a first control signal operative to induce an initial tourniquet pressure in the cuff means higher than the minimum blood pressure required to maintain a bloodless field and subsequently to provide a second control signal operative to induce a tourniquet pressure lower than said initial tourniquet pressure in the cuff means and suitable for maintaining the bloodless field; and control apparatus for determining an operative pressure of said variable pressure cuff means as the product of blood pressure and a factor and including means for monitoring the blood pressure of a patient, the operative pressure being included in at least one of said first and second control signals.

2. An automatic tourniquet system according to claim 1, wherein the blood pressure used for determining is a weighted combination of the systolic and diastolic blood pressures.

3. An automatic tourniquet system according to claim 2, wherein said weighted combination is the mean blood pressure.

4. An automatic tourniquet system according to claim 1, wherein said factor is selected according to at least one of the following:
   the limb or artery on which said cuff means is mounted;
   the size of the cuff means; and
   whether the patient is an adult or a child.

5. An automatic tourniquet system according to claim 1, wherein said control apparatus includes means for causing said cuff means to apply an initial pressure which is at least twice the blood pressure for a predetermined limited time.

6. An automatic tourniquet system according to claim 5, wherein said initial pressure is a constant for a limb/artery.

7. An automatic tourniquet system according to claim 5, wherein said predetermined limited time is less than 10 minutes.

8. An automatic tourniquet system according to claim 1, wherein said means for monitoring comprise means for measuring the systolic and diastolic pressure.

9. An automatic tourniquet method comprising the steps of:
   applying a variable pressure to a limb or artery of a patient in order to occlude blood flow thereat by using variable pressure cuff means;
   providing a first control signal operative to induce an initial tourniquet pressure in the cuff means higher than the minimum blood pressure required to maintain a bloodless field and subsequently to provide a second control signal operative to induce a tourniquet pressure lower than said initial tourniquet pressure in the cuff means and suitable for maintaining the bloodless field; and
   determining an operative pressure of said variable pressure cuff means as the product of blood pressure and a factor, by monitoring the blood pressure of a patient, the operative pressure being included in at least one of said first and second control signals.

10. An automatic tourniquet method according to claim 9, wherein the blood pressure used in the determining step is a weighted combination of the systolic and diastolic blood pressures.

11. An automatic tourniquet method according to claim 10, wherein said weighted combination is the mean blood pressure.

12. An automatic tourniquet method according to claim 9, further comprising the step of selecting said factor based on the limb or artery on which said cuff means is mounted.

13. An automatic tourniquet method according to claim 9, wherein said determining step includes causing said cuff means to apply an initial pressure which is at least twice the blood pressure for a determined limited time.

14. An automatic tourniquet method according to claim 13, wherein said initial pressure is a constant for a limb/artery.

15. An automatic tourniquet method according to claim 13, wherein said predetermined limited time is less than 10 minutes.

16. An automatic tourniquet method according to claim 9, wherein said monitoring step comprises measuring the systolic and diastolic blood pressure.

17. An automatic tourniquet method comprising the steps of:
   applying a variable pressure to a limb or artery of a patient in order to occlude blood flow thereat by using variable pressure cuff means;
   providing a first control signal operative to induce an initial tourniquet pressure in the cuff means higher than the minimum blood pressure required to maintain a bloodless field and subsequently to provide a second control signal operative to induce a tourniquet pressure lower than said initial tourniquet pressure in the cuff means and suitable for maintaining the bloodless field; and
   automatically performing an IV regional anesthesia by using a proximal cuff and distal cuff and a cuff inflation/deflation device by the step of:
   controlling the cuff inflation/deflation device according to a proximal and distal inflation and deflation schedule, whereby the method operates automatically in accordance with a predetermined schedule.

18. An automatic tourniquet method according to claim 17, wherein the schedule comprises the steps of:
   a. in response to a user's signal, inflating the proximal cuff until a particular relatively high cuff pressure is reached,
   b. allowing the high cuff pressure of the proximal cuff to decrease,
   c. once a particular relatively low cuff pressure is reached, maintaining a low cuff pressure in the proximal cuff,
   d. in response to a user's signal, inflating the distal cuff until a particular relatively high cuff pressure is reached,
   e. allowing the high cuff pressure of the distal cuff to decrease,
   f. once a particular relatively low cuff pressure is reached, maintaining the low cuff pressure in the distal cuff,
   g. after the relatively high cuff pressure is reached in the distal cuff, entirely deflating the proximal cuff, and
   h. in response to a user's signal, on-and-off deflating the distal cuff.

19. An automatic tourniquet method according to claim 17, wherein the distal cuff deflation schedule comprises the steps of alternating inflations and deflations of the distal cuff.

20. An automatic tourniquet method according to claim 17, further comprising the step of determining the inflation and deflation schedule according to at least one user input.

21. An automatic tourniquet method according to claim 20, wherein the at least one user input includes at least one of the following: determination of a relatively high pressure for at least one of the distal and proximal cuffs, indication of a limb/artery, cuff size.

22. An automatic tourniquet system in combination with an apparatus for automatically performing an IV regional anesthesia comprising: variable pressure cuff means for applying a variable pressure to a limb or artery of a patient in order to occlude blood flow thereat including a proximal cuff and a distal cuff and a cuff inflation/deflation device, a double tourniquet cuff control unit for controlling the cuff inflation/deflation which is connected to the cuff means and which is operative to provide a first control signal operative to induce an initial tourniquet pressure in the proximal cuff higher than the minimum blood pressure required to maintain a bloodless field and subsequently to provide a second control signal operative to induce a tourniquet pressure lower than said initial tourniquet pressure in the proximal cuff and suitable for maintaining the bloodless field, said double cuff pressure control further being operative for controlling the proximal and distal cuff inflation/deflation device according to a predetermined schedule, whereby the apparatus operates automatically in accordance with a predetermined schedule.

23. An automatic tourniquet method comprising the steps of:

applying a variable pressure to a limb or artery of a patient in order to occlude blood flow thereat by using variable pressure cuff means;

providing a first control signal operative to induce an initial tourniquet pressure in the cuff means higher than the minimum blood pressure required to maintain a bloodless field;

providing a second control signal operative to induce a tourniquet pressure lower than the initial tourniquet pressure in the cuff means and that maintains the bloodless field; and maintaining the bloodless field for so long as a tourniquet is to be applied to the limb or artery for its intended purpose.

24. An automatic tourniquet method according to claim 23 further comprising the steps of controlling inflation and deflation of two or more adjacent ones of the cuff means, and providing control signals for:

a. inflating the first cuff;

b. inflating the second cuff after a predetermined or user-selected time interval;

c. once the second cuff is inflated, deflating the first cuff, thereby relieving pressure on the first cuff body site;

d. after a predetermined or user-selected time interval, inflating the first cuff; and e. once the first cuff is inflated, deflating the second cuff, thereby relieving pressure on the second cuff body site.

* * * * *